(12) United States Patent
Lennon et al.

(10) Patent No.: US 11,224,546 B2
(45) Date of Patent: Jan. 18, 2022

(54) FINE HOLLOW FIBERS HAVING A HIGH VOID FRACTION

(71) Applicant: Kimberly-Clark Worldwide, Inc., Neenah, WI (US)

(72) Inventors: Eric E. Lennon, Roswell, GA (US); John H. Conrad, Alpharetta, GA (US); Douglas J. Hulslander, Stone Mountain, GA (US); David W. Hall, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 719 days.

(21) Appl. No.: 15/517,561

(22) PCT Filed: Dec. 10, 2015

(86) PCT No.: PCT/US2015/064871
§ 371 (c)(1),
(2) Date: Apr. 7, 2017

(87) PCT Pub. No.: WO2016/100057
PCT Pub. Date: Jun. 23, 2016

(65) Prior Publication Data
US 2017/0304128 A1    Oct. 26, 2017

Related U.S. Application Data

(60) Provisional application No. 62/094,166, filed on Dec. 19, 2014.

(51) Int. Cl.
*A61F 13/511* (2006.01)
*D04H 3/007* (2012.01)
(Continued)

(52) U.S. Cl.
CPC ...... *A61F 13/51121* (2013.01); *A61F 13/511* (2013.01); *A61F 13/514* (2013.01);
(Continued)

(58) Field of Classification Search
CPC .......................... B29C 48/05; A61F 13/51121
See application file for complete search history.

(56) References Cited

U.S. PATENT DOCUMENTS

| 3,338,992 A | 8/1967 | Kinney |
| 3,341,394 A | 9/1967 | Kinney |

(Continued)

FOREIGN PATENT DOCUMENTS

| EP | 2 677 074 A1 | 12/2013 |
| JP | 61289110 A † | 12/1986 |

(Continued)

OTHER PUBLICATIONS

International Search Report and Written Opinion for PCT/US2015/064871 dated Mar. 22, 2016, 13 pages.
(Continued)

*Primary Examiner* — Larry W Thrower
(74) *Attorney, Agent, or Firm* — Dority & Manning, P.A.

(57) ABSTRACT

A hollow fiber that extending along at least a portion of the fiber along a longitudinal axis thereof and is defined by an interior wall is provided. Through selective control over the manner in which it is formed, the present inventors have discovered that the hollow fiber can exhibit a unique combination of a high void fraction and small fiber size that makes it particularly suitable for use in certain applications, such as in nonwoven webs for absorbent articles.

11 Claims, 4 Drawing Sheets

(51) Int. Cl.
| | | |
|---|---|---|
| *D04H 3/011* | (2012.01) | |
| *D04H 3/018* | (2012.01) | |
| *D01D 5/24* | (2006.01) | |
| *D04H 3/009* | (2012.01) | |
| *D01F 8/06* | (2006.01) | |
| *D01F 6/04* | (2006.01) | |
| *A61F 13/514* | (2006.01) | |
| *D04H 1/4391* | (2012.01) | |
| *A61L 15/24* | (2006.01) | |
| *D01D 5/08* | (2006.01) | |
| *D04H 1/4291* | (2012.01) | |
| *D04H 1/435* | (2012.01) | |
| *A61F 13/51* | (2006.01) | |

(52) U.S. Cl.
CPC ........ *A61F 13/51401* (2013.01); *A61L 15/24* (2013.01); *D01D 5/08* (2013.01); *D01D 5/24* (2013.01); *D01F 6/04* (2013.01); *D01F 8/06* (2013.01); *D04H 1/4291* (2013.01); *D04H 1/435* (2013.01); *D04H 1/43914* (2020.05); *D04H 3/007* (2013.01); *D04H 3/009* (2013.01); *D04H 3/011* (2013.01); *D04H 3/018* (2013.01); *A61F 2013/51009* (2013.01); *A61F 2013/51026* (2013.01)

(56) References Cited

U.S. PATENT DOCUMENTS

| | | | |
|---|---|---|---|
| 3,502,538 | A | 3/1970 | Petersen |
| 3,502,763 | A | 3/1970 | Hartmann |
| 3,542,615 | A | 11/1970 | Dobo et al. |
| 3,692,618 | A | 9/1972 | Dorschner et al. |
| 3,802,817 | A | 4/1974 | Matsuki et al. |
| 3,849,241 | A | 11/1974 | Butin et al. |
| 3,855,046 | A | 12/1974 | Hansen et al. |
| 4,041,203 | A | 8/1977 | Brock et al. |
| 4,340,563 | A | 7/1982 | Appel et al. |
| 4,374,888 | A | 2/1983 | Bornslaeger |
| 4,704,116 | A | 11/1987 | Enloe |
| 4,766,029 | A | 8/1988 | Brock et al. |
| 4,798,603 | A | 1/1989 | Meyer et al. |
| D315,990 | S | 4/1991 | Blenke et al. |
| 5,169,706 | A | 12/1992 | Collier, IV et al. |
| 5,192,606 | A | 3/1993 | Proxmire et al. |
| 5,213,881 | A | 5/1993 | Timmons et al. |
| 5,248,309 | A | 9/1993 | Serbiak et al. |
| 5,382,400 | A | 1/1995 | Pike et al. |
| D358,035 | S | 5/1995 | Zander et al. |
| 5,464,688 | A | 11/1995 | Timmons et al. |
| 5,486,166 | A | 1/1996 | Bishop et al. |
| 5,490,846 | A | 2/1996 | Ellis et al. |
| 5,539,056 | A | 7/1996 | Yang et al. |
| 5,558,659 | A | 9/1996 | Sherrod et al. |
| 5,571,619 | A | 11/1996 | McAlpin et al. |
| 5,585,182 | A | 12/1996 | Aneja et al. |
| 5,596,052 | A | 1/1997 | Resconi et al. |
| 5,620,779 | A | 4/1997 | Levy et al. |
| 5,643,660 | A | 7/1997 | Price et al. |
| D384,508 | S | 10/1997 | Zander et al. |
| D384,819 | S | 10/1997 | Zander et al. |
| 5,702,377 | A | 12/1997 | Collier, IV et al. |
| D390,708 | S | 2/1998 | Brown |
| 5,766,389 | A | 6/1998 | Brandon et al. |
| 5,843,057 | A | 12/1998 | McCormack |
| 5,855,999 | A | 1/1999 | McCormack |
| 5,931,823 | A | 8/1999 | Stokes et al. |
| 5,932,497 | A | 8/1999 | Morman et al. |
| 5,962,112 | A | 10/1999 | Haynes et al. |
| 5,997,981 | A | 12/1999 | McCormack et al. |
| 6,002,064 | A | 12/1999 | Kobylivker et al. |
| D418,305 | S | 1/2000 | Zander et al. |
| 6,015,764 | A | 1/2000 | McCormack et al. |
| 6,037,281 | A | 3/2000 | Mathis et al. |
| 6,060,638 | A | 5/2000 | Paul et al. |
| D428,267 | S | 7/2000 | Romano, III et al. |
| 6,093,665 | A | 7/2000 | Sayovitz et al. |
| 6,111,163 | A | 8/2000 | McCormack et al. |
| 6,150,002 | A | 11/2000 | Varona |
| 6,461,457 | B1 | 10/2002 | Taylor et al. |
| 6,500,563 | B1 | 12/2002 | Datta et al. |
| 6,663,611 | B2 | 12/2003 | Blaney et al. |
| 7,060,867 | B2 | 6/2006 | Jameson |
| 7,172,398 | B2 | 2/2007 | Bentley et al. |
| 8,652,476 | B2 | 2/2014 | Shimohata et al. |
| 9,139,935 | B2 | 9/2015 | Chen et al. |
| 9,439,961 | B2 | 9/2016 | Shimohata et al. |
| 2004/0002273 | A1 | 1/2004 | Fitting et al. |
| 2005/0054255 | A1 | 3/2005 | Morman et al. |
| 2005/0059941 | A1 | 3/2005 | Baldwin et al. |
| 2011/0136402 | A1 | 6/2011 | Matsubara et al. |
| 2011/0264235 | A1* | 10/2011 | Chen .................. B01D 69/08 623/23.72 |
| 2012/0088424 | A1* | 4/2012 | Eric .................. D04H 1/4291 442/400 |
| 2013/0317469 | A1 | 11/2013 | Matsubara et al. |

FOREIGN PATENT DOCUMENTS

| | | |
|---|---|---|
| JP | S 61-289110 A | 12/1986 |
| JP | 2009174098 | 8/2009 |
| WO | WO 00/44411 A1 | 8/2000 |
| WO | 2004003271 A1 † | 1/2004 |
| WO | WO 2004/003271 A1 | 1/2004 |
| WO | WO 2006/033118 A1 | 3/2006 |
| WO | WO201151273 | 5/2011 |

OTHER PUBLICATIONS

Catalogue of Kazan Nozzle Mfg. Co., Ltd. Published Jul. 2016, 3 pages.
Third Party Observation dated Apr. 30, 2018, 10 pages.
Supplementary European Search Report dated Jun. 1, 2018, 9 pages.

\* cited by examiner
† cited by third party

FINE HOLLOW FIBERS HAVING A HIGH VOID FRACTION

RELATED APPLICATION

The present application is the national stage entry of International Patent Application No. PCT/US2015/064871 having a filing date of Dec. 10, 2015, which claims priority to U.S. Patent Application Ser. No. 62/094,166 filed on Dec. 19, 2014, which are incorporated herein in their entirety by reference thereto.

BACKGROUND OF THE INVENTION

Fibrous materials are used in a wide variety of different components to help control the flow of fluids. In absorbent articles, for instance, fibrous materials (e.g., nonwoven webs) can be used to rapidly absorb bodily fluids (e.g., urine) and allow them to flow into an absorbent layer without permitting or facilitating re-transmission of the fluids to the wearer. Unfortunately, fibrous materials can experience multiple problems when used in this manner. For example, it is often desirable to lower the basis weight of the fibrous material to allow for the formation of thinner products. With most conventional fibrous materials, however, such a reduction in basis weight can adversely impact other properties, such as liquid strikethrough and barrier properties. While some solutions to these problems have been proposed, none are fully satisfactory. For example, U.S. Pat. No. 6,368,990 describes a spunbond nonwoven web that is formed from hollow filaments or staple fibers. According to the '990 patent, such hollow fibers can allow for a lower basis weight or an increase in the number of fibers for a given basis weight. Despite achieving some improvement, these hollow fibers still suffer from multiple deficiencies. For example, the fibers tend to lack a high enough void fraction to significantly improve the fluid intake properties of the material beyond what is already conventional. Further, attempts to increase the void fraction unfortunately tend to result in an increase in the overall diameter of the fiber, which is not desirable for most applications.

As such, a need currently exists for improved hollow fibers for use in various applications.

SUMMARY OF THE INVENTION

In accordance with one embodiment of the present invention, a hollow fiber is disclosed that generally extends in a longitudinal direction and has an average fiber diameter. The hollow fiber comprises a hollow cavity that extends along at least a portion of the fiber in the longitudinal direction and is defined by an interior wall. The interior wall has an average thickness and the product of the average thickness and the average fiber diameter is about 110 square micrometers or less and wherein the fiber has a void fraction that is from about 5% to about 50%.

In accordance with another embodiment of the present invention, a spinneret for forming a hollow fiber is disclosed. The spinneret contains a spin plate that defines a plurality of capillaries having one or more spaced apart slots, wherein at least a portion of the slots have a width and length such that the ratio of the length to the width is greater than about 5. The width of the slots is from about 0.08 to about 0.2 millimeters. The slots further have an outer diameter that is defined as the distance between outer edges of the slots, the outer diameter being greater than about 0.6 millimeters. The total open area defined by the slots within a capillary is likewise from about 0.10 to about 0.40 square millimeters.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF REPRESENTATIVE EMBODIMENTS

Definitions

As used herein, the term "fiber" generally refers to an elongated extrudate formed by passing a polymer through a forming orifice, such as a die. Unless noted otherwise, the term "fiber" includes both discontinuous fibers having a definite length and substantially continuous filaments. Substantially filaments may, for instance, have a length much greater than their diameter, such as a length to diameter ratio ("aspect ratio") greater than about 15,000 to 1, and in some cases, greater than about 50,000 to 1. The fiber is "hollow" to such an extent that it contains a hollow cavity extending along at least a portion of the fiber in the longitudinal direction. In some cases, the cavity may extent along the entire length of the fiber.

As used herein the term "nonwoven web" generally refers to a web having a structure of fibers that are interlaid, but not in an identifiable manner as in a knitted fabric. Examples of suitable nonwoven webs include, but are not limited to, meltblown webs, spunbond webs, bonded carded webs, airlaid webs, coform webs, hydraulically entangled webs, and so forth.

As used herein, the term "spunbond" web generally refers to a nonwoven web containing substantially continuous filaments formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al.

As used herein, the term "meltblown" web or facing generally refers to a nonwoven web containing fibers formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a fiber that contains a hollow cavity extending along at least a portion of the fiber along a longitudinal axis thereof and is defined by an interior wall. Through selective control over the manner in which it is formed, the present inventors have discovered that the hollow fiber can exhibit a unique combination of a high void fraction and small fiber size that makes it particularly suitable for use in certain applications, such as in nonwoven webs for absorbent articles. One parameter that is particularly representative of this property is the product of the average diameter of the fiber and its average wall thickness, which is relatively small for the hollow fibers of the present invention. That is, the product is typically about 110 square micrometers or less, in some embodiments about 100 square micrometers or less, and in some embodiments, from about 20 to about 90 square micrometers. The interior wall may, for example, have an average wall thickness of from about 3 to about 10 micrometers, in some embodiments from about 3.25 to about 9.75 micrometers, and in some embodiments from about 3.35 to about 9.25 micrometers. Likewise, the average diameter of the fiber, which may or may not be the same as the outer diameter of the interior wall, may be from about range from about 5 to about 30 micrometers, in some embodiments from about 10 to about 25 micrometers, and in some embodiments, from about 15 to about 20 micrometers. It should be understood that the actual wall thickness and diameter values may vary somewhat along the longitudinal axis of the fiber. Nevertheless, one benefit of the present invention is that such values may remain relatively constant such that the coefficient of variation in wall thickness and/or diameter is about 35% or less, in some embodiments about 30% or less, and in some embodiments, from about 10% to about 25% along the longitudinal direction of the fiber. The void fraction of the fiber may also be relatively high, such as from about 5% to about 50%, in some embodiments from about 8% to about 40%, in some embodiments from about 10% to about 30%, and in some embodiments, from about 15% to about 25%. Void fraction may be determined by microscopy (e.g., optical or SEM). The void fraction is determined by dividing the area of the voided portion by the area of the entire fiber (void and fiber) and then multiplying by 100.

The unique hollow fibers of the present invention are formed using a process in which a thermoplastic composition is extruded through a spinneret. The thermoplastic composition contains at least one polymer and optionally at least one additive. Suitable thermoplastic polymers may include, for instance, polyesters (e.g., polylactic acid, polyethylene terephthalate, etc.); polyolefins (e.g., polyethylene, polypropylene, polybutylene, etc.); polytetrafluoroethylene; polyvinyl acetates; polyvinyl chloride acetates; polyvinyl butyrals; acrylic resins (e.g., polyacrylate, polymethylacrylate, polymethylmethacrylate, etc.); polyamides (e.g., nylon); polyvinyl chlorides; polyvinylidene chlorides; polystyrene;s polyvinyl alcohols; polyurethanes; and so forth. In one embodiment, for instance, the thermoplastic composition may be a polyolefin composition to the extent that polyolefins constitute from about 50 wt. % to about 99 wt. %, in some embodiments from about 60 wt. % to about 98 wt. %, and in some embodiments, from about 80 wt. % to about 95 wt. % of the thermoplastic composition. The polyolefins may have a melting temperature of from about 100° C. to about 220° C., in some embodiments from about 120° C. to about 200° C., and in some embodiments, from about 140° C. to about 180° C. The melting temperature may be determined using differential scanning calorimetry ("DSC") in accordance with ASTM D-3417. Suitable polyolefins may, for instance, include ethylene polymers (e.g., low density polyethylene ("LDPE"), high density polyethylene ("HDPE"), linear low density polyethylene ("LLDPE"), etc.), propylene homopolymers (e.g., syndiotactic, atactic, isotactic, etc.), propylene copolymers, and so forth.

In one particular embodiment, the polyolefin is a propylene homopolymer or copolymer (e.g., random or block) containing about 10 wt. % or less of co-monomers (e.g., α-olefins), and in some embodiments, about 2 wt. % or less. If desired, the propylene polymer may be syndiotactic or isotactic. The term "syndiotactic" generally refers to a tacticity in which a substantial portion, if not all, of the methyl groups alternate on opposite sides along the polymer chain. On the other hand, the term "isotactic" generally refers to a tacticity in which a substantial portion, if not all, of the methyl groups are on the same side along the polymer chain. Such polymers are typically formed using a Ziegler-Natta catalyst, either alone or in combination with a small amount of an α-olefin co-monomer. Isotactic polymers, for instance, typically have a density in the range of from 0.90 to 0.94 g/cm$^3$, such as determined in accordance with ASTM 1505-10. Commercially available propylene homopolymers may include, for instance, Metocene™ MF650Y and MF650X (BaseII Polyolefins); PP2252E1, PP 3155 or PP 2252 (ExxonMobil); and M3661 PP (Total Refining and Chemicals). Other examples of suitable propylene polymers may be described in U.S. Pat. No. 6,500,563 to Datta, et al.; U.S. Pat. No. 5,539,056 to Yang, et al.; and U.S. Pat. No. 5,596,052 to Resconi, et al.

Of course, other polyolefins may also be employed in the composition of the present invention, either alone or in combination with the polymers noted above. For example, the polyolefin may be a copolymer of propylene with another α-olefin, such as a $C_3$-$C_{20}$ α-olefin or $C_3$-$C_{12}$ α-olefin. Specific examples of suitable α-olefins include ethylene, 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are ethylene, 1-butene, 1-hexene and 1-octene. Suitable propylene copolymers include those commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich.

Other additives may also be incorporated into the composition, such as slid aids (e.g., fatty acid derivatives) melt stabilizers, processing stabilizers, heat stabilizers, light stabilizers, antioxidants, heat aging stabilizers, whitening agents, antiblocking agents, bonding agents, tackifiers, viscosity modifiers, etc.

In certain embodiments, the fiber may be a monocomponent fiber such that the interior wall is formed entirely by the thermoplastic composition, which may contain at least one polymer and optionally at least one additive. Of course, in other embodiments, the fiber may contain one or more additional polymer layers as a component (e.g., bicomponent) to further enhance strength, processibility, and/or other properties. Such fibers may, for example, have a sheath-core configuration, side-by-side configuration, segmented pie configuration, island-in-the-sea configuration, and so forth.

Figure 4:
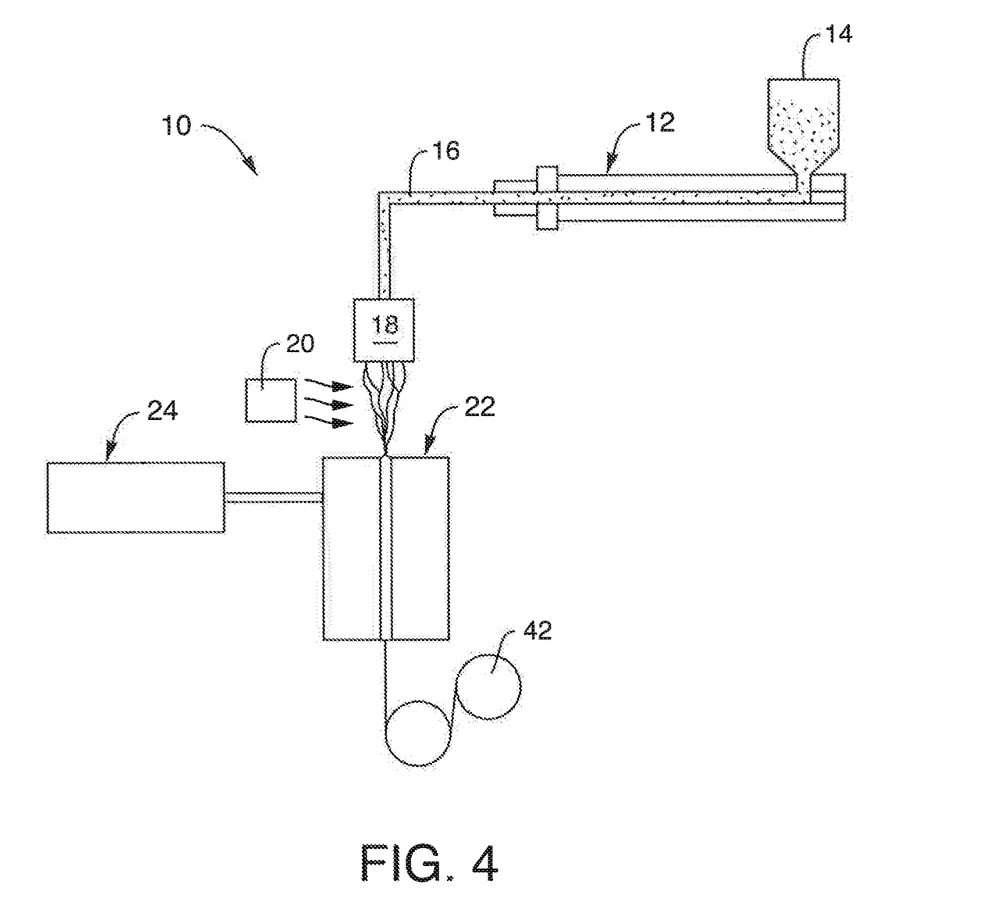
FIG. 4 is a schematic illustration of a process that may be used in one embodiment of the present invention to form hollow fibers.
Figure 5:
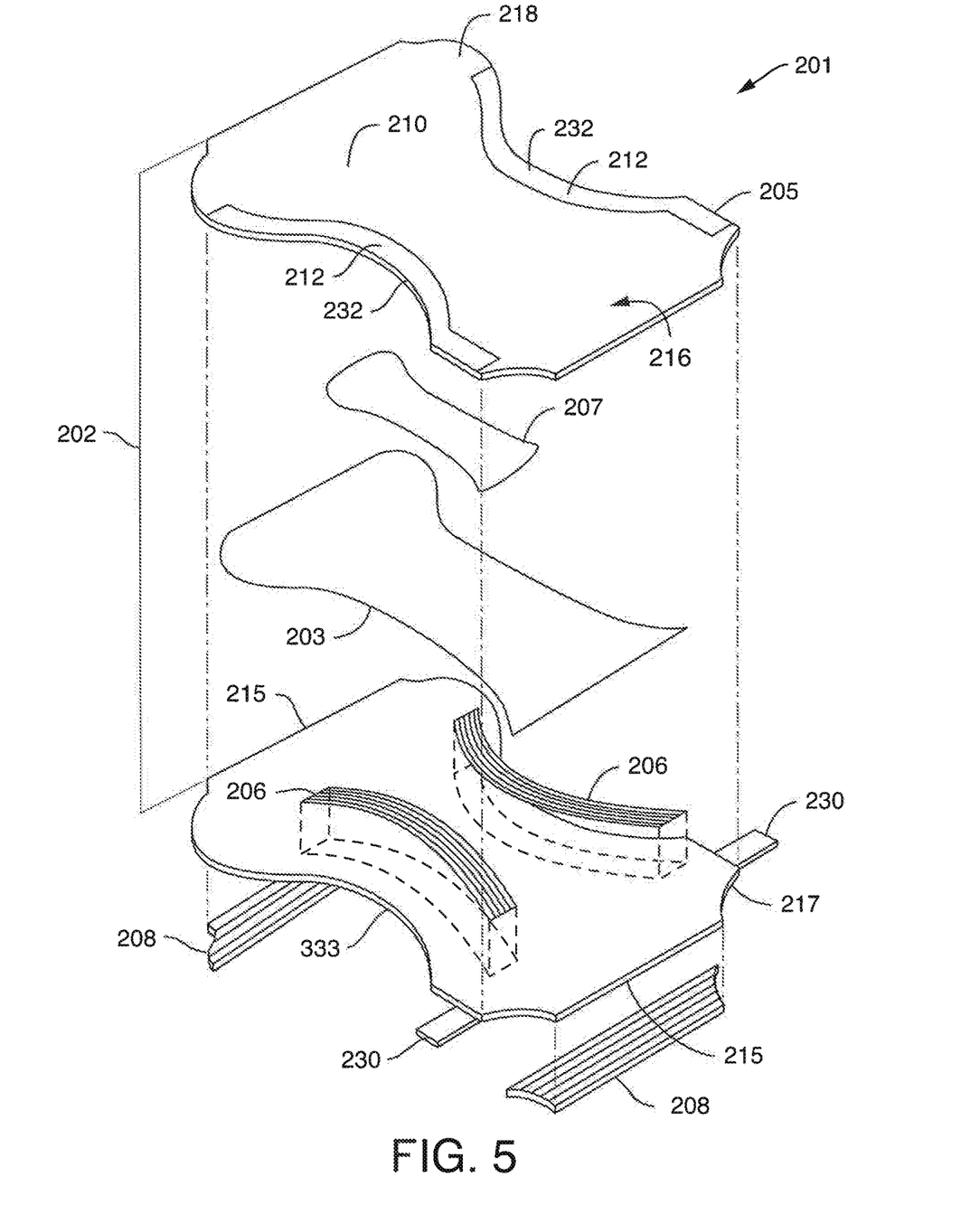
FIG. 5 is one embodiment of an absorbent article that can employ the hollow fibers of the present invention.

Regardless of the particular composition and configuration employed, the method for forming the hollow fibers is selectively controlled in the present invention to achieve the desired combination of a high void fraction and small fiber size. Referring to FIG. 4, for example, one embodiment of a method for forming fibers is shown in more detail. In this particular embodiment, a thermoplastic composition may be fed into an extruder 12 from a hopper 14. The blend may be provided to the hopper 14 using any conventional technique. The extruder 12 is heated to a temperature sufficient to extrude the melted polymer. To help limit deterioration of the hollow cavity as it is formed, the composition is typically melt spun at a temperature of from about 180° C. to about 300° C., in some embodiments from about 200° C. to about 260° C., and in some embodiments, from about 210° C. to about 250° C.

The extruded composition is then passed through a polymer conduit 16 to a spinneret 18. Notably, the present inventors have discovered that the particular nature of the spinneret can be selectively controlled to help achieve the desired fiber properties noted above. More particularly, the spinneret may contain at least one spin plate that defines a plurality of capillaries having one more shaped slots (or segments) through which the thermoplastic composition can flow. For example, the slots may have a multi-directional shape, such as a C-shape, arc-shape, etc., so that the thermoplastic composition forms a bulge when passed therethrough, thus causing it to coalesce a short distance below the face of the die and form a fiber with a hollow interior.

Figure 1:
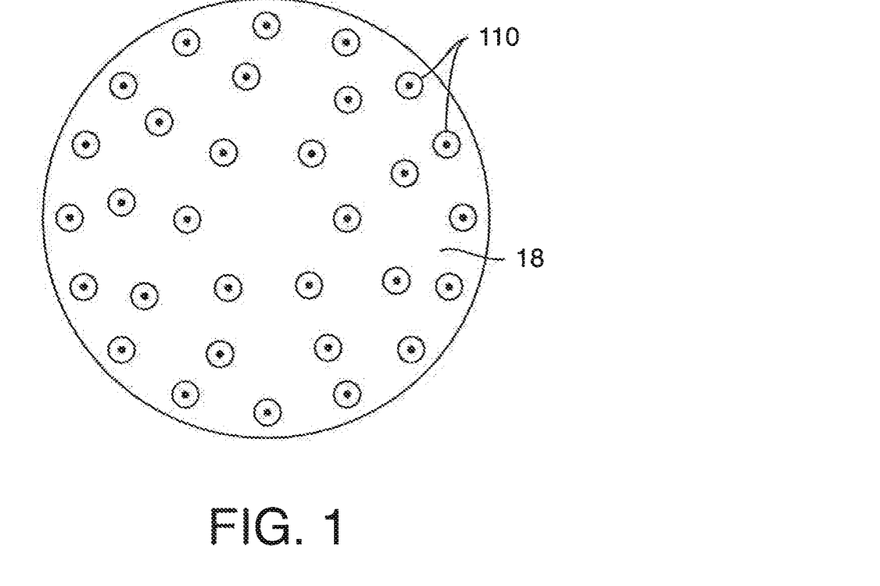
FIG. 1 is a top view of one embodiment of the spinneret of the present invention, which may be employed to form hollow fibers.
Figure 2:
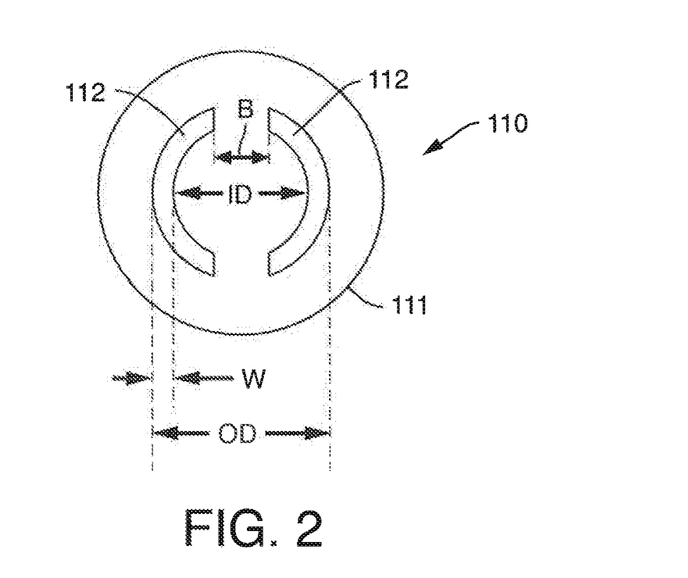
FIG. 2 is a top view of a capillary shown in the spinneret of FIG. 1.
Figure 3:
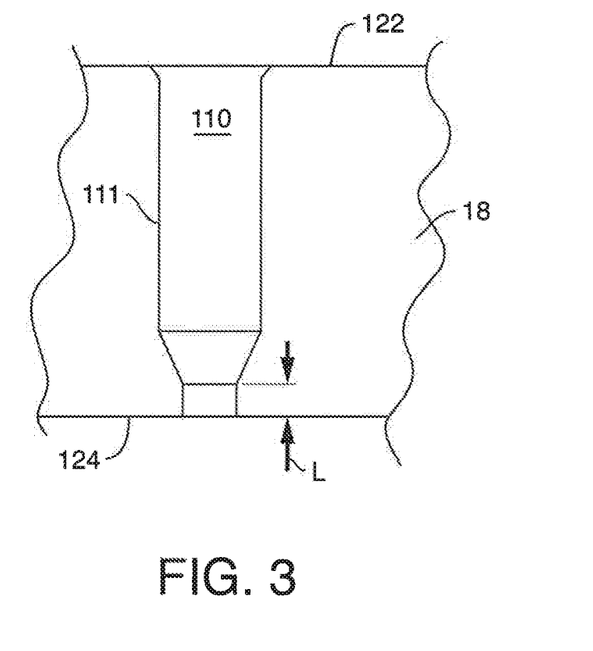
FIG. 3 is a cross-sectional view of the capillary of FIG. 2.

Referring to FIGS. 1-3, for instance, one embodiment a spinneret 18 is shown that can be used to form hollow fibers of the present invention. As illustrated, the spinneret 18 contains a plurality of capillaries 110 that extend through a spin plate from an upper surface 122 to a face 124 (FIG. 3). Any suitable number of slots may be employed, such as from 2 to 10 slots, in some embodiments from 2 to 6 slots, and in some embodiments, from 2 to 4 slots. In this particular embodiment, for instance, the capillaries 110 contain two C-shaped slots 112 having a width "W" (FIG. 2) and a length "L" (FIG. 3). The present inventors have discovered that through selective control over the ratio of the length to the width of the slots, hollow fibers can be produced having the desired void fraction and wall thickness. For instance, the ratio of the length to width is typically greater than about 5, in some embodiments from about 6 to about 100, and in some embodiments, from about 8 to about 80. The width may, for instance, range from about 0.08 to about 0.2 millimeters, in some embodiments from about 0.09 to about 0.18 millimeters, and in some embodiments, from about 0.10 to about 0.15 millimeters. The length may likewise range from about 0.4 to about 2.0 millimeters, in some embodiments from about 0.5 to about 1.8 millimeters, and in some embodiments, from about 0.8 to about 1.5 millimeters. Although the width and length are shown as being relatively constant in the embodiment of FIGS. 1-3, it should be understood that such values can vary if so desired. For instance, the slot may have an irregular shape so that its width varies along its length, or vice versa. In such cases, the average width and/or length values may nevertheless be controlled to fall within the ranges noted above.

Other parameters of the capillary and slot configuration may also be selectively controlled in the present invention to achieve the desired hollow fiber properties. For instance, the outer diameter of the slots 112, which is designated as "OD" in FIG. 2 and is the distance between the outer edges of each slot 112, is typically greater than about 0.6 millimeters, in some embodiments greater than about 0.7 millimeters, in some embodiments, from about 0.8 millimeters to about 10 millimeters, and in some embodiments, from about 0.9 to about 5 millimeters. The inner diameter "ID" of the capillary 110 may likewise be from about 0.2 millimeters to about 2.0 millimeters, in some embodiments, from about 0.3 millimeters to about 1.8 millimeters, and in some embodiments, from about 0.4 to about 1.4 millimeters. The distance "B" between the ends of the slots may also vary, such as from about 0.01 to about 0.5 millimeters, in some embodiments from about 0.01 to about 0.4 millimeters, and in some embodiments, from about 0.05 to about 0.2 millimeters. In addition, the total open area defined by the slots within a capillary is likewise typically from about 0.10 to about 0.40 square millimeters, in some embodiments from about 0.12 to about 0.38 square millimeters, and in some embodiments, from about 0.14 to about 0.35 square millimeters. The total open area may be calculated using the following equation:

$$\text{Total Open Area} = (0.25\pi OD^2) - (0.25\pi ID^2) - (B*W*N)$$

wherein,
OD is the outer diameter of the capillary;
ID is the inner diameter of the capillary;
B is the distance between ends of the slots;
W is the width of the slots; and
N is the number of slots.

Referring again to FIG. 4, the spinneret 18 can produce a downwardly extruding curtain of hollows when the thermoplastic composition is extruded therethrough. Once formed, a blower 20 may be employed that quenches the fibers. The quench air may be directed from one side of the fiber curtain as shown in FIG. 4 or both sides of the fiber curtain. To form a fiber with the desired length, the quenched fibers are generally melt drawn, such as using a fiber draw unit 22 as shown in FIG. 4. Fiber draw units or aspirators for use in melt spinning polymers are well-known in the art. Suitable fiber draw units for use in the process of the present invention include a linear fiber aspirator of the type shown in U.S. Pat. Nos. 3,802,817 and 3,423,255. The fiber draw 22 generally includes an elongated vertical passage through which the fibers are drawn by aspirating air entering from the sides of the passage and flowing downwardly through the passage. A heater or blower 24 supplies aspirating air to the fiber draw unit 22. The aspirating air melt draws the fibers and ambient air through the fiber draw unit 22. The flow of gas causes the fibers to melt draw or attenuate, which increases the molecular orientation or crystallinity of the polymers forming the fibers. When employing a fiber draw unit, the "draw down" ratio may be selected to help achieve the desired fiber length. The "drawn down" ratio is the linear speed of the fibers after drawing (e.g., linear speed of the godet roll 42 or a foraminous surface (not shown) divided by the linear speed of the fibers after extrusion). In certain embodiments, the draw down ratio may be from about 20:1 to about 4000:1, in some embodiments from about 25:1 to about 2000:1, and in some embodiments, from about 50:1 to about 1000:1 and in some embodiments from about 75:1 to about 800:1.

Once formed, the fibers may be deposited through the outlet opening of the fiber draw unit 22 and onto a godet roll 42. If desired, the fibers collected on the godet roll 42 may optionally be subjected to additional in line processing and/or converting steps (not shown) as will be understood by those skilled in the art. For example, fibers may be collected and thereafter crimped, texturized, and/or and cut to an average fiber length in the range of from about 3 to about 80 millimeters, in some embodiments from about 4 to about 65 millimeters, and in some embodiments, from about 5 to about 50 millimeters. The staple fibers may then be incorporated into a nonwoven web as is known in the art, such as bonded carded webs, through-air bonded webs, etc.

The resulting hollow fibers of the present invention possess can be suitably employed in various applications without first being formed into any type of coherent structure. Nevertheless, in certain cases, it may be desired to form the fibers into a coherent nonwoven web structure by randomly depositing the fibers onto a forming surface (optionally with the aid of a vacuum) and then bonding the resulting web using any known technique. The nonwoven web may be formed before or after the fibers are drawn. In certain embodiments, for instance, it may be desired to form a nonwoven web from a plurality of fibers, and thereafter draw the fibers by stretching the nonwoven web to the extent desired to form the porous network. In an alternative embodiment, an endless forming surface may simply be positioned below a fiber aspiration unit that draws the fibers to the desired extent before the web is formed.

Once formed, the nonwoven web may then be bonded using any conventional technique, such as with an adhesive or autogenously (e.g., fusion and/or self-adhesion of the fibers without an applied external adhesive). Autogenous bonding, for instance, may be achieved through contact of the fibers while they are semi-molten or tacky, or simply by blending a tackifying resin and/or solvent with the polymer used to form the fibers. Suitable autogenous bonding techniques may include ultrasonic bonding, thermal bonding, through-air bonding, calendar bonding, and so forth. For example, the web may be further bonded or embossed with a pattern by a thermo-mechanical process in which the web is passed between a heated smooth anvil roll and a heated pattern roll. The pattern roll may have any raised pattern which provides the desired web properties or appearance. Desirably, the pattern roll defines a raised pattern which defines a plurality of bond locations which define a bond area between about 2% and 30% of the total area of the roll. Exemplary bond patterns include, for instance, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et al., as well as U.S. Design Pat. Nos. 428,267 to Romano et al.; 390,708 to Brown; 418,305 to Zander, et al.; 384,508 to Zander, et al.; 384,819 to Zander, et al.; 358,035 to Zander, et al.; and 315,990 to Blenke, et al. The pressure between the rolls may be from about 5 to about 2000 pounds per lineal inch. The pressure between the rolls and the temperature of the rolls is balanced to obtain desired web properties or appearance while maintaining cloth like properties. As is well known to those skilled in the art, the temperature and pressure required may vary depending upon many factors including but not limited to, pattern bond area, polymer properties, fiber properties and nonwoven properties.

If desired, the nonwoven web may also be a composite that contains a combination of the hollow fibers of the present invention and other types of fibers (e.g., staple fibers, filaments, etc.). For example, additional synthetic fibers may be utilized, such as those formed from polyolefins, e.g., polyethylene, polypropylene, polybutylene, and so forth; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; etc. If desired, renewable polymers may also be employed. Some examples of known synthetic fibers include sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del. Polylactic acid staple fibers may also be employed, such as those commercially available from Far Eastern Textile, Ltd. of Taiwan.

The composite may also contain pulp fibers, such as high-average fiber length pulp, low-average fiber length pulp, or mixtures thereof. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas fir, true firs, pine (e.g., southern pines), spruce (e.g., black spruce), bamboo, combinations thereof, and so forth. Northern softwood kraft pulp fibers may be used in the present invention. An example of commercially available southern softwood kraft pulp fibers suitable for use in the present invention include those available from Weyerhaeuser Company with offices in Federal Way, Washington under the trade designation of "NF-405." Another suitable pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, eucalyptus, maple, birch, aspen, etc. Eucalyptus kraft pulp fibers may be particularly desired to increase softness, enhance brightness, increase opacity, and change the pore structure of the sheet to increase its wicking ability. Bamboo or cotton fibers may also be employed.

Nonwoven laminates may also be formed in the present invention in which one or more layers are formed from the hollow fibers. For example, the nonwoven web of one layer may be a spunbond that contains the hollow fibers, while the nonwoven web of another layer may contain other types of fibers. In one embodiment, the nonwoven laminate contains a meltblown layer positioned between two spunbond layers to form a spunbond/meltblown/spunbond ("SMS") laminate. If desired, the spunbond layer(s) may be formed from the hollow fibers. Various techniques for forming SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., as well as U.S. Patent Application Publication No. 2004/0002273 to Fitting, et al. Of course, the nonwoven laminate may have other configuration and possess any desired number of meltblown and spunbond layers, such as spunbond/meltblown/meltblown/spunbond laminates ("SMMS"), spunbond/meltblown laminates ("SM"), etc. Although the basis weight of the nonwoven laminate may be tailored to the desired application, it generally ranges from about 10 to about 300 grams per square meter ("gsm"), in some embodiments from about 25 to about 200 gsm, and in some embodiments, from about 40 to about 150 gsm.

Nonwoven-film laminates may also be formed. In such embodiments, the film is typically liquid-impermeable and either vapor-permeable or vapor-impermeable. Films that are liquid-impermeable and vapor-permeable are often referred to as "breathable" and they typically have a water vapor transmission rate ("WVTR") of about 100 grams per square meter per 24 hours ($g/m^2/24$ hours) or more, in some embodiments from about 500 to about 20,000 $g/m^2/24$ hours, and in some embodiments, from about 1,000 to about 15,000 g $g/m^2/24$ hours. The breathable film may also be a microporous or monolithic film. Microporous films are typically formed by incorporating a filler (e.g., calcium carbonate) into the polymer matrix, and thereafter stretching the film to create the pores. Examples of such films are described, for instance, in U.S. Pat. No. 5,843,057 to McCormack; U.S. Pat. No. 5,855,999 to McCormack; U.S. Pat. No. 5,932,497 to Morman, et al.; U.S. Pat. No. 5,997,981 to McCormack, et al.; U.S. Pat. No. 6,002,064 to Kobylivker, et al.; U.S. Pat. No. 6,015,764 to McCormack, et al.; U.S. Pat. No. 6,037,281 to Mathis, et al.; U.S. Pat. No. 6,111,163 to McCormack, et al.; and U.S. Pat. No. 6,461,457 to Taylor, et al.

The hollow fibers of the present invention may be employed in a wide variety of different articles. For instance, the hollow fibers may be employed in an absorbent article. An absorbent article that is capable of absorbing water or other fluids. Examples of some absorbent articles include, but are not limited to, personal care absorbent articles, such as diapers, training pants, absorbent underpants, adult incontinence articles, feminine hygiene products (e.g., sanitary napkins), swim wear, baby wipes, mitt wipes, and so forth; medical absorbent articles, such as garments, fenestration materials, underpads, bandages, absorbent drapes, and medical wipes; food service wipers; clothing articles; and so forth. Regardless of the intended application, the absorbent article typically contains an absorbent member (e.g., core layer, surge layer, transfer delay layer, wrapsheet, ventilation layer, etc.) positioned between a backsheet and a topsheet. Notably, the absorbent member, backsheet, and/or topsheet, as well one or more other components of the absorbent article (e.g., ears, containment flaps, side panels, waist or leg bands, etc.) may include the hollow fibers of the present invention, either alone or in the form of a nonwoven web containing such fibers.

In this regard, various exemplary embodiments of the absorbent article will be described. Referring to FIG. 1, for instance, one particular embodiment of an absorbent article 201 is shown in the form of a diaper. However, as noted above, the invention may be embodied in other types of absorbent articles, such as incontinence articles, sanitary napkins, diaper pants, feminine napkins, training pants, and so forth. In the illustrated embodiment, the absorbent article 201 is shown as having an hourglass shape in an unfastened configuration. However, other shapes may of course be utilized, such as a generally rectangular shape, T-shape, or I-shape. As shown, the absorbent article 201 includes a chassis 202 formed by various components, including a backsheet 217, topsheet 205, and absorbent member that includes an absorbent core layer 203 and surge layer 207. It should be understood, however, that other layers may also be used in the present invention. Likewise, one or more of the layers referred to in FIG. 1 may also be eliminated in certain embodiments of the present invention.

As indicated above, the backsheet 217 may contain the hollow fibers of the present invention, optionally in the form of a nonwoven web. For example, the nonwoven web may be positioned so that it defines a garment-facing surface 333 of the absorbent article 201. The absorbent article 201 also includes a topsheet 205. The topsheet 205 is generally designed to contact the body of the user and is liquid-permeable. For example, the topsheet 205 may define a body-facing surface 218, which is typically compliant, soft feeling, and non-irritating to the wearers skin. If desired, the topsheet 205 may contain the hollow fibers of the present invention, optionally in the form of a nonwoven web. For example, a nonwoven web may be positioned so that it defines the body-facing surface 218 if so desired. The topsheet may surround the absorbent core layer 203 so that it completely encases the absorbent article. Alternatively, the topsheet 205 and the backsheet 217 may extend beyond the absorbent member and be peripherally joined together, either entirely or partially, using known techniques, such as by adhesive bonding, ultrasonic bonding, etc. As indicated above, the topsheet 205 may include the nonwoven web of the present invention. The topsheet 205 may also include a conventional a nonwoven web (e.g., spunbond web, meltblown web, or bonded carded web). Other exemplary topsheet constructions that contain a nonwoven web are described in U.S. Pat. Nos. 5,192,606; 5,702,377; 5,931,823; 6,060,638; and 6,150,002, as well as U.S. Patent Application Publication Nos. 2004/0102750, 2005/0054255, and 2005/0059941. The topsheet 205 may also contain a plurality of apertures formed therethrough to permit body fluid to pass more readily into the absorbent core layer 203. The apertures may be randomly or uniformly arranged throughout the topsheet 205, or they may be located only in the narrow longitudinal band or strip arranged along the longitudinal axis of the absorbent article. The apertures permit rapid penetration of body fluid down into the absorbent member. The size, shape, diameter and number of apertures may be varied to suit one's particular needs.

The absorbent article also contains an absorbent member positioned between the topsheet and the backsheet. The absorbent member may be formed from a single absorbent layer or a composite containing separate and distinct absorbent layer. It should be understood, however, that any number of absorbent layers may be utilized in the present invention. In FIG. 1, for instance, the absorbent member contains an absorbent core layer 203 and a surge layer 207 that helps to decelerate and diffuse surges or gushes of liquid that may be rapidly introduced into the absorbent core layer 203. Desirably, the surge layer 207 rapidly accepts and temporarily holds the liquid prior to releasing it into the storage or retention portions of the absorbent core layer 203. In the illustrated embodiment, for example, the surge layer 207 is interposed between an inwardly facing surface 216 of the topsheet 205 and the absorbent core layer 203. Alternatively, the surge layer 207 may be located on the outwardly facing surface 218 of the topsheet 205. The surge layer 207 is typically constructed from highly liquid-permeable materials. Suitable materials may include porous woven materials, porous nonwoven materials, and apertured films. In one embodiment, the surge layer 207 may contain the hollow fibers of the present invention, optionally in the form of a nonwoven web. Other examples of suitable surge layers are described in U.S. Pat. No. 5,486,166 to Ellis, et al. and U.S. Pat. No. 5,490,846 to Ellis, et al.

If desired, the absorbent member may also contain a transfer delay layer positioned vertically below the surge layer. The transfer delay layer may contain a material that is less hydrophilic than the other absorbent layers, and may generally be characterized as being substantially hydrophobic. For example, the transfer delay layer may be a nonwoven web (e.g., spunbond web) formed from the hollow fibers of the present invention. The fibers may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer are described in U.S. Pat. No. 4,798,603 to Meyer, et al. and U.S. Pat. No. 5,248,309 to Serbiak, et al. To adjust the performance of the invention, the transfer delay layer may also be treated with a selected amount of surfactant to increase its initial wettability.

The transfer delay layer may generally have any size, such as a length of about 150 mm to about 300 mm. Typically, the length of the transfer delay layer is approximately equal to the length of the absorbent article. The transfer delay layer may also be equal in width to the surge layer, but is typically wider. For example, the width of the transfer delay layer may be from between about 50 mm to about 75 mm, and particularly about 48 mm. The transfer delay layer typically has a basis weight less than that of the other absorbent members. For example, the basis weight of the transfer delay layer is typically less than about 150 grams per square meter (gsm), and in some embodiments, between about 10 gsm to about 100 gsm. If desired, the transfer delay layer may contain the hollow fibers of the present invention, optionally in the form of a nonwoven web.

Besides the above-mentioned components, the absorbent article 201 may also contain various other components as is known in the art. For example, the absorbent article 201 may also contain a substantially hydrophilic wrapsheet (not illustrated) that helps maintain the integrity of the fibrous structure of the absorbent core layer 203. The wrapsheet is typically placed about the absorbent core layer 203 over at least the two major facing surfaces thereof, and composed of an absorbent cellulosic material, such as creped wadding or a high wet-strength tissue. The wrapsheet may be configured to provide a wicking layer that helps to rapidly distribute liquid over the mass of absorbent fibers of the absorbent core layer 203. The wrapsheet material on one side of the absorbent fibrous mass may be bonded to the wrapsheet located on the opposite side of the fibrous mass to effectively entrap the absorbent core layer 203. Furthermore, the absorbent article 201 may also include a ventilation layer (not shown) that is positioned between the absorbent core layer 203 and the backsheet 217. When utilized, the ventilation layer may help insulate the backsheet 217 from the absorbent core layer 203, thereby reducing dampness in the backsheet 217. Examples of such ventilation layers may include a nonwoven web laminated to a breathable film, such as described in U.S. Pat. No. 6,663,611 to Blaney, et al. If desired, the wrapsheet and/or ventilation layer may contain the hollow fibers of the present invention, optionally in the form of a nonwoven web.

In some embodiments, the absorbent article 201 may also include a pair of ears (not shown) that extend from the side edges 232 of the absorbent article 201 into one of the waist regions. The ears may be integrally formed with a selected diaper component. For example, the ears may be integrally formed with the backsheet 217 or from the material employed to provide the top surface, which may include the hollow fibers of the present invention, optionally in the form of a nonwoven web. In alternative configurations, the ears may be provided by members connected and assembled to the backsheet 217, the top surface, between the backsheet 217 and top surface, or in various other configurations. As noted above, the ears may contain the hollow fibers of the present invention, optionally in the form of a nonwoven web.

As representatively illustrated in FIG. 1, the absorbent article 201 may also include a pair of containment flaps 212 that are configured to provide a barrier and to contain the lateral flow of body exudates. The containment flaps 212 may be located along the laterally opposed side edges 232 of the topsheet 205 adjacent the side edges of the absorbent core layer 203. The containment flaps 212 may extend longitudinally along the entire length of the absorbent core layer 203, or may only extend partially along the length of the absorbent core layer 203. When the containment flaps 212 are shorter in length than the absorbent core layer 203, they may be selectively positioned anywhere along the side edges 232 of absorbent article 201 in a crotch region 210. In one embodiment, the containment flaps 212 extend along the entire length of the absorbent core layer 203 to better contain the body exudates. Such containment flaps 212 are generally well known to those skilled in the art. For example, suitable constructions and arrangements for the containment flaps 212 are described in U.S. Pat. No. 4,704,116 to Enloe. If desired, the containment flaps may contain the hollow fibers of the present invention, optionally in the form of a nonwoven web.

The absorbent article 201 may include various elastic or stretchable materials, such as a pair of leg elastic members 206 affixed to the side edges 232 to further prevent leakage of body exudates and to support the absorbent core layer 203. In addition, a pair of waist elastic members 208 may be affixed to longitudinally opposed waist edges 215 of the absorbent article 201. The leg elastic members 206 and the waist elastic members 208 are generally adapted to closely fit about the legs and waist of the wearer in use to maintain a positive, contacting relationship with the wearer and to effectively reduce or eliminate the leakage of body exudates from the absorbent article 201. The absorbent article 201 may also include one or more fasteners 230. For example, two flexible fasteners 130 are illustrated in FIG. 1 on opposite side edges of waist regions to create a waist opening and a pair of leg openings about the wearer. The shape of the fasteners 230 may generally vary, but may include, for instance, generally rectangular shapes, square shapes, circular shapes, triangular shapes, oval shapes, linear shapes, and so forth. The fasteners may include, for instance, a hook material. In one particular embodiment, each fastener 230 includes a separate piece of hook material affixed to the inside surface of a flexible backing. The elastic members (e.g., leg, waist, etc.) and/or fasteners may contain the hollow fibers of the present invention if desired, optionally in the form of a nonwoven web.

The various regions and/or components of the absorbent article 201 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the backsheet 217 and topsheet 205 are assembled to each other and to the absorbent core layer 203 using an adhesive. Alternatively, the absorbent core layer 203 may be connected to the backsheet 217 using conventional fasteners, such as buttons, hook and loop type fasteners, adhesive tape fasteners, and so forth. Similarly, other diaper components, such as the leg elastic members 206, waist elastic members 208 and fasteners 230, may also be assembled into the absorbent article 201 using any attachment mechanism.

Although various configurations of a diaper have been described above, it should be understood that other diaper and absorbent article configurations are also included within the scope of the present invention. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth.

The present invention may be better understood with reference to the following examples.

Example 1

A spinneret was configured to form hollow fibers. The spinneret contained 2,612 capillaries having an outer diameter of 1 millimeter. The capillaries contained four (4) slots having a width ("W") of 0.10 millimeters, an end distance ("B") of 0.24 millimeters, and a length ("L") of 1.2 millimeters. The total open area was thus calculated to be 0.19 square millimeters and the length to width ratio of the slots was 8. A propylene homopolymer (Exxon Mobil 3155 PP) was supplied to the spinneret at a melt temperature of 450° F. to produce fibers at a rate of 0.52 grams per hole per minute. The resulting fibers had an average diameter of 18.1 micrometers, an average wall thickness of 5.3 micrometers, and a void fraction of 17.2%. Nonwoven webs were also produced from these fibers with basis weights ranging from 0.30 to 0.43 ounces per square yard. The product of the average wall thickness and the average diameter was 95.4 square micrometers.

Example 2

A spinneret was configured to form hollow fibers. The spinneret contained 2,612 capillaries having an outer diameter of 1 millimeter. The capillaries contained two (2) slots having a width ("W") of 0.10 millimeters, an end distance ("B") of 0.18 millimeters, and a length ("L") of 1.2 millimeters. The total open area was thus calculated to be 0.25 square millimeters and the length to width ratio of the slots was 8. A propylene homopolymer (Exxon Mobil 3155 PP) was supplied to the spinneret at a melt temperature of 450° F. to produce fibers at a rate of 0.52 grams per hole per minute. The resulting fibers had an average diameter of 18.5 micrometers, an average wall thickness of 5.2 micrometers, and a void fraction of 19.5%. Nonwoven webs were also produced from these fibers with basis weights ranging from 0.28 to 0.45 ounces per square yard. The product of the average wall thickness and the average diameter was 93.6 square micrometers.

Example 3

Two spinnerets were configured to form hollow fibers. Each spinneret contained 20,350 capillaries having an outer diameter of 1 millimeter. The capillaries contained two (2) slots having a width ("W") of 0.15 millimeters, an end distance ("B") of 0.18 millimeters, and a length ("L") of 1.2 millimeters. The total open area was thus calculated to be 0.35 square millimeters and the length to width ratio of the slots was 8. A propylene homopolymer (Exxon Mobil 3155 PP) was supplied to the spinneret at a melt temperature of 445-455° F. to produce fibers at a rate of 0.52 grams per hole per minute. The resulting fibers had an average diameter of 15.8 micrometers, an average wall thickness of 5.7 micrometers, and a void fraction of 8.0%. Nonwoven webs were also produced from these fibers with basis weights ranging from 0.37 to 0.44 ounces per square yard. The product of the average wall thickness and the average diameter was 90.06 square micrometers.

Comparative Example 1

A spinneret was configured to form hollow fibers. The spinneret contained 12 capillaries having an outer diameter of 1.34 millimeter. The capillaries contained two (2) slots having a width ("W") of 0.15 millimeters, an end distance ("B") of 0.18 millimeters, and a length ("L") of 1.2 millimeters. The total open area was thus calculated to be 0.51 square millimeters and the length to width ratio of the slots was 8. A propylene homopolymer (Exxon Mobil 3155 PP) was supplied to the spinneret at a melt temperature of 450° F. to produce fibers at a rate of 0.60 grams per hole per minute. The resulting fibers had an average diameter of 21.3 micrometers, an average wall thickness of 5.3 micrometers, and a void fraction of 25.2%. The product of the average wall thickness and the average diameter was 112.89 square micrometers.

Comparative Example 2

A spinneret was configured to form hollow fibers. The spinneret contained 12 capillaries having an outer diameter of 1.0 millimeter. The capillaries contained two (2) slots having a width ("W") of 0.25 millimeters, an end distance ("B") of 0.18 millimeters, and a length ("L") of 1.2 millimeters. The total open area was thus calculated to be 0.50 square millimeters and the length to width ratio of the slots was 8. A propylene homopolymer (Exxon Mobil 3155 PP) was supplied to the spinneret at a melt temperature of 450° F. to produce fibers at a rate of 0.60 grams per hole per minute. The resulting fibers had an average diameter of 25.6 micrometers, an average wall thickness of 9.9 micrometers, and a void fraction of 5.0%. The product of the average wall thickness and the average diameter was 253.44 square micrometers.

Comparative Example 3

A spinneret was configured to form hollow fibers. The spinneret contained 12 capillaries having an outer diameter of 1.0 millimeter. The capillaries contained two (2) slots having a width ("W") of 0.20 millimeters, an end distance ("B") of 0.18 millimeters, and a length ("L") of 1.5 millimeters. The total open area was thus calculated to be 0.43 square millimeters and the length to width ratio of the slots was 8. A propylene homopolymer (Exxon Mobil 3155 PP) was supplied to the spinneret at a melt temperature of 450° F. to produce fibers at a rate of 0.60 grams per hole per minute. The resulting fibers had an average diameter of 20.8 micrometers, an average wall thickness of 7.8 micrometers, and a void fraction of 6.2%. The product of the average wall thickness and the average diameter was 162.86 square micrometers.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An extruded hollow fiber that generally extends in a longitudinal direction and has an average fiber diameter of from 5 micrometers to 30 micrometers, the hollow fiber comprising a hollow cavity that extends along at least a portion of the fiber in the longitudinal direction and is defined by an interior wall, wherein the interior wall has an average thickness and the product of the average thickness and the average fiber diameter is 110 square micrometers or less and wherein the fiber has a void fraction that is from 5% to 50%.

2. The extruded hollow fiber of claim 1, wherein the average thickness of the interior wall is from 3 to 10 micrometers.

3. The extruded hollow fiber of claim 1, wherein the average fiber diameter is from 10 micrometers to 25 micrometers.

4. The extruded hollow fiber of claim 1, wherein the interior wall is formed from a thermoplastic polyolefin composition.

5. The extruded hollow fiber of claim 1, wherein the fiber is a monocomponent fiber formed from a thermoplastic composition.

6. The extruded hollow fiber of claim 5, wherein the thermoplastic composition contains at least one polymer and optionally at least one additive.

7. The extruded hollow fiber of claim 1, wherein the fiber is a bicomponent fiber.

8. A nonwoven web comprising the extruded hollow fiber of claim 1.

9. An absorbent article comprising the nonwoven web of claim 8 wherein the absorbent article includes a substantially liquid-impermeable layer, liquid-permeable layer, and an absorbent core, wherein the substantially liquid-impermeable layer, the liquid-permeable layer, or both include the nonwoven web.

10. The extruded hollow fiber of claim 1, wherein the fiber is formed from polyethylene, polypropylene, or combination thereof.

11. The extruded hollow fiber of claim 10, wherein the fiber is formed from a polypropylene homopolymer or copolymer.

* * * * *